US008788872B2

(12) United States Patent
Drucker et al.

(10) Patent No.: US 8,788,872 B2
(45) Date of Patent: *Jul. 22, 2014

(54) MANAGING FAILOVER OPERATIONS ON A CLUSTER OF COMPUTERS

(71) Applicant: International Business Machines Corporation, Armonk, NY (US)

(72) Inventors: Travis M. Drucker, Rochester, MN (US); Joel C. Dubbels, Eyota, MN (US); Thomas J. Eggebraaten, Rochester, MN (US); Janice R. Glowacki, Rochester, MN (US); Richard J. Stevens, Rochester, MN (US); David A. Wall, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/689,170

(22) Filed: Nov. 29, 2012

(65) Prior Publication Data
US 2013/0097457 A1 Apr. 18, 2013

Related U.S. Application Data

(63) Continuation of application No. 13/275,394, filed on Oct. 18, 2011.

(51) Int. Cl.
*G06F 11/00* (2006.01)

(52) U.S. Cl.
USPC .............................................. 714/2; 714/4.11

(58) Field of Classification Search
USPC .................. 714/2, 4.1, 4.11, 6.3, 6.32, 10–13
See application file for complete search history.

(56) References Cited

U.S. PATENT DOCUMENTS

| 2002/0112196 A1* | 8/2002 | Datta et al. ................... 714/4 |
| 2004/0210656 A1* | 10/2004 | Beck et al. ................. 709/225 |
| 2005/0229021 A1* | 10/2005 | Lubbers et al. ............... 714/2 |
| 2009/0265710 A1 | 10/2009 | Shen et al. |
| 2010/0011177 A1 | 1/2010 | Ainscow et al. |
| 2010/0070796 A1 | 3/2010 | Sivaperuman et al. |
| 2012/0072397 A1 | 3/2012 | Esaka |
| 2013/0097456 A1 | 4/2013 | Drucker et al. |

OTHER PUBLICATIONS

Office Action, U.S. Appl. No. 13/275,394, Sep. 4, 2013, 1-4.
Combined Search and Examination Report mailed Feb. 19, 2013.
Notice of Allowance, U.S. Appl. No. 13/275,394, Dec. 24, 2013, pp. 1-4.

* cited by examiner

*Primary Examiner* — Dieu-Minh Le
(74) *Attorney, Agent, or Firm* — Biggers Kennedy Lenart Spraggins LLP

(57) ABSTRACT

Managing failover operations on a cluster of computers, including: identifying, by a failover hold module, a failure to access data storage in the cluster of computers; preventing the execution of all read operations directed to the data storage that were received after the failure to access data storage was identified; executing all write operations directed to the data storage that were received after the failure to access data storage was identified, including writing data to a cache; identifying that a failover to alternative data storage is complete; executing the held read operations, including reading data from the alternative data storage; and copying, from cache to the alternative data storage, the data written to the cache as part of the write operations.

9 Claims, 9 Drawing Sheets

Medical Image Business Object 118

Request ID 302
Request Type 304
Action ID 306
Provider ID 308
Patient ID 310
Physician ID 312
Technician ID 314
Scanner ID 316
Scanner Type 318
Image ID 320
Image Type 322
Patient Location 324
Destination Location 326
Receiving Gateway ID 328
Destination Gateway ID 330

Original Image Pointer 332
Interim Image Pointer 334
Resultant Image Pointer 336

Image Provider Protocol 338

FIG. 3

MANAGING FAILOVER OPERATIONS ON A CLUSTER OF COMPUTERS

CROSS-REFERENCE TO RELATED APPLICATION

This application is a continuation application of and claims priority from U.S. patent application Ser. No. 13/275,394, filed on Oct. 18, 2011.

BACKGROUND OF THE INVENTION

1. Field of the Invention

The field of the invention is data processing, or, more specifically, methods, apparatus, and products for managing failover operations on a cluster of computers.

2. Description of Related Art

Current medical image management systems are inflexible and do not support a model of accessing any and all medical images produced across a multi-facility enterprise. This causes the data from analyzing these images to be difficult to share and difficult to produce.

SUMMARY OF THE INVENTION

Methods and apparatus for managing failover operations on a cluster of computers, including: identifying, by a failover hold module, a failure to access data storage in the cluster of computers; preventing the execution of all read operations directed to the data storage that were received after the failure to access data storage was identified; executing all write operations directed to the data storage that were received after the failure to access data storage was identified, including writing data to a cache; identifying that a failover to alternative data storage is complete; executing the held read operations, including reading data from the alternative data storage; and copying, from cache to the alternative data storage, the data written to the cache as part of the write operations.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

BRIEF DESCRIPTION OF THE DRAWINGS

FIG. 3 sets forth a block diagram of an example medical image business object according to embodiments of the present invention.

DETAILED DESCRIPTION OF EXEMPLARY EMBODIMENTS

Figure 1:
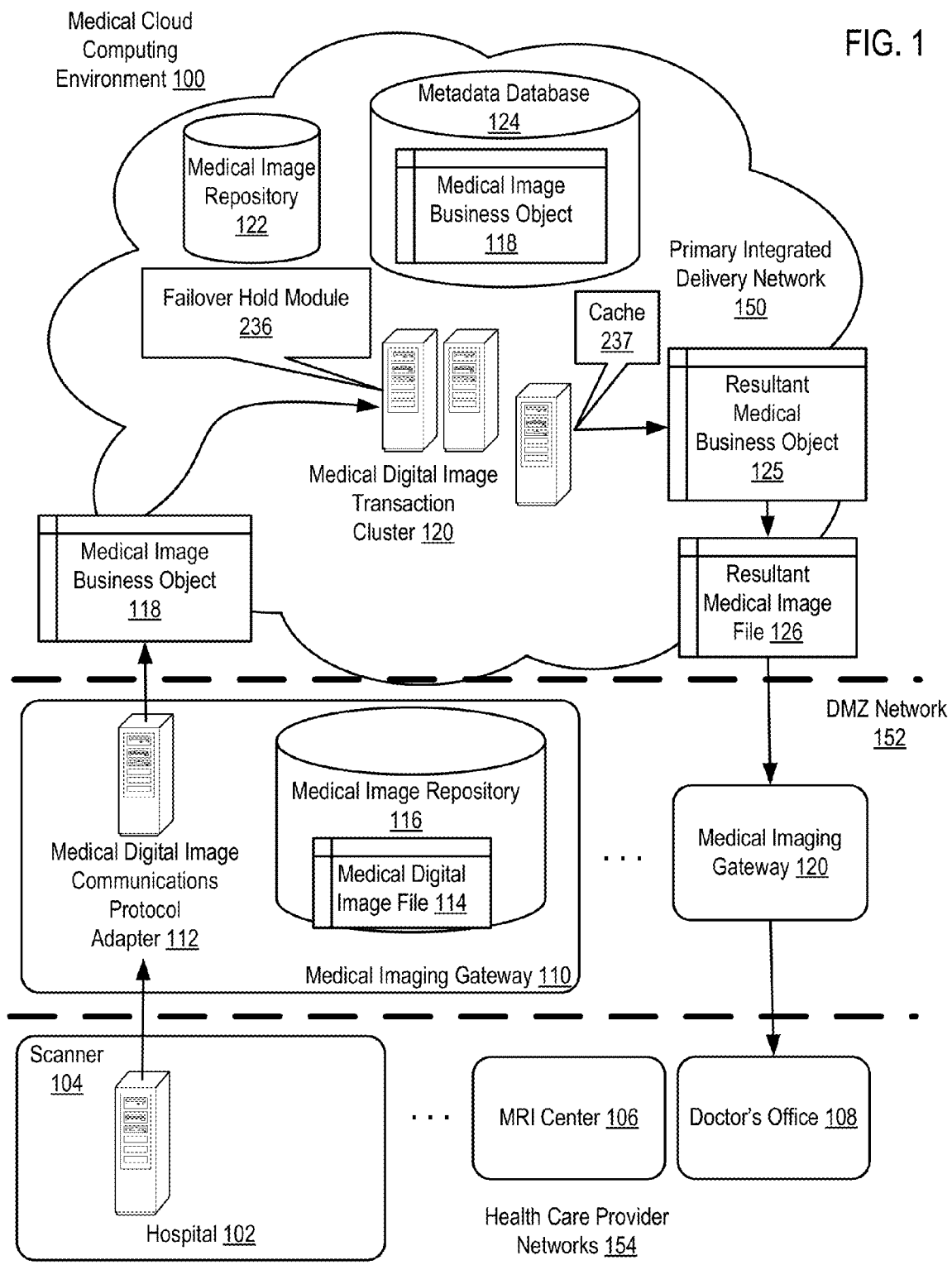
FIG. 1 sets forth a network diagram of a system for administering a medical digital images in a distributed medical digital image computing environment and managing failover operations according to embodiments of the present invention.

Exemplary methods, systems, and products for administering a business transaction in accordance with the present invention are described with reference to the accompanying drawings, beginning with FIG. 1. FIG. 1 sets forth a network diagram of a system for administering medical digital images in a distributed medical digital image computing environment and managing failover operations according to embodiments of the present invention. The system of FIG. 1 includes a distributed processing system implemented as a medical cloud computing environment (100). Cloud computing is a model of service delivery for enabling convenient, often on-demand network access to a shared pool of configurable computing resources.

Examples of computing resources that may be accessed include computer networks, network bandwidth, servers, processing capabilities, computer memory, software applications, virtual machines, and services that can be rapidly provisioned and released with reduced management effort or interaction with the provider of the service. Cloud models can include five characteristics, three service models, or four deployment models.

Characteristics of the cloud model can include on-demand self-service, broad network access, resource pooling, rapid elasticity, and measured service. On-demand self-service is a characteristic in which a cloud consumer can unilaterally provision computing capabilities, such as server time and network storage, as needed automatically without requiring human interaction with the cloud service provider.

Broad network access is a characteristic describing capabilities that are available over a network. The capabilities may be accessed through standard mechanisms that promote use by heterogeneous thin or thick client platforms such as mobile phones, laptops, desktop computers, PDAs, and so on as will occur to those of skill in the art.

Resource pooling is a characteristic in which the cloud service provider's computing resources are pooled to serve multiple consumers using a multi-tenant model, with different physical and virtual resources dynamically assigned and reassigned according to demand. There may be a sense of location independence in that the consumer generally has no control or knowledge over the exact location of the provided resources but may be able to specify a location at a higher level of abstraction such as the country, state, datacenter and so on.

Rapid elasticity is a characteristic in which the capabilities of the cloud computing environment can be rapidly and elastically provisioned, in some cases automatically, to quickly scale out and rapidly released to quickly scale in. To the consumer of the cloud computing environment, the capabilities available for provisioning often appear to be unlimited and appear to be able to be purchased in any quantity at any time. Measured service is a characteristic in which cloud systems automatically control and optimize resource use by leveraging a metering capability at some level of abstraction appropriate to the type of service such as storage, processing, bandwidth, active user accounts, and so on. Resource usage can be monitored, controlled, and reported providing transparency for both the provider and consumer of the utilized service.

Cloud models can include three service models. Examples of service models implemented in the cloud computing environment can include software as a service ('SaaS'), platform as a service ('PaaS') and infrastructure as a service ('IaaS'). SaaS typically provides the capability to the consumer to use the provider's applications running on a cloud infrastructure. The applications can be accessible from various client devices through a thin client interface such as a web browser, web-based e-mail client, and so on. The consumer may not manage or control the underlying cloud infrastructure including network, servers, operating systems, storage, or even individual application capabilities, with the common possible exception of limited user-specific application configuration settings.

PaaS typically includes the capability provided to the consumer to deploy onto the cloud infrastructure consumer-created or acquired applications created using programming languages and tools supported by the cloud service provider. The consumer often does not manage or control the underlying cloud infrastructure including networks, servers, operating systems, or storage, but has control over the deployed applications and possibly application hosting environment configurations.

IaaS typically includes the capability provided to consumers to provision processing, storage, networks, and other fundamental computing resources where the consumers are able to deploy and run arbitrary software, which can include operating systems and applications. The consumers often do not manage or control the underlying cloud infrastructure but have control over operating systems, storage, deployed applications, and possibly limited control of select networking components such as, for example, host firewalls.

Cloud models can include four deployment models. Example deployment models used in cloud computing environments can include private clouds, community clouds, public clouds, and hybrid clouds. In a private cloud deployment model, the cloud infrastructure can be operated solely for an organization. The cloud infrastructure may be managed by the organization or a third party and may exist on-premises or off-premises. In the community cloud deployment model, the cloud infrastructure is shared by several organizations and supports a specific community that has shared concerns such as, for example, mission, security requirements, policy, compliance considerations, and so on. The cloud infrastructure may be managed by the organizations or a third party and may exist on-premises or off-premises. In the public cloud deployment model, the cloud infrastructure is made available to the general public or a large industry group and is owned by an organization selling cloud services. In the hybrid cloud deployment model, the cloud infrastructure is a composition of two or more clouds, such as private, community, public, that remain unique entities but are bound together by standardized or proprietary technology that enables data and application portability such as, for example, cloud bursting for load-balancing between clouds.

A cloud computing environment is generally considered service oriented with a focus on statelessness, low coupling, modularity, and semantic interoperability. At the heart of cloud computing is an infrastructure comprising a network of interconnected nodes. The distributed processing computing environment of FIG. 1 includes a medical imaging cloud computing environment (100). The medical imaging cloud computing environment (100) of FIG. 1 is capable of administering medical digital images according to embodiments of the present invention. In the example of FIG. 1 the medical imaging cloud computing environment (100) includes two networks: a primary integrated delivery network (150) and a DMZ network (152). The primary integrated delivery network (150) of FIG. 1 is a highly secure network for administering image processing transactions upon medical images according to aspects of embodiments of the present invention. The DMZ network (152), or demilitarized zone, of FIG. 1 is a physical or logical subnetwork that contains and exposes the medical imaging cloud computing environment's external services to the larger untrusted network, such as the Internet, through which the health care provider networks (154) may access the services of the medical imaging cloud computing environment. The DMZ network (152) of FIG. 1 adds an additional layer of security to the medical imaging cloud because an external attacker only has access to equipment in the DMZ, rather than any other part of the medical imaging cloud.

The medical cloud computing environment (100) of FIG. 1 includes medical imaging cloud gateway (110) in the DMZ network (152). The medical imaging cloud gateway (110) in the DMZ network (152) includes a medical digital image communications protocol adapter (112). The medical digital image communications protocol adapter (112) may be embodied as a module of automated computing machinery that is capable of receiving a medical digital image from a provider of medical images. Providers of medical images can include a hospital (102), an MRI center (106), a doctor's office, and others as will occur to those of skill in the art. The medical digital image communications protocol adapter (112) is capable of receiving the medical image according to any number of protocols supported by the providers of the medical images such as Digital Imaging and Communications in Medicine ('DICOM'), Health Level Seven ('HL7'), and others as will occur to those of skill in the art.

DICOM is a standard for handling, storing, printing, and transmitting information in medical imaging. DICOM includes a file format definition and a network communications protocol. The communication protocol is an application protocol that uses TCP/IP to communicate between systems. DICOM files can be exchanged between two entities that are capable of receiving image and patient data in DICOM format. DICOM enables the integration of scanners, X-ray machines, cameras, ultrasound machines, servers, workstations, printers, and network hardware from multiple manufacturers into a picture archiving and communication system ('PACS'). HL7 is an all-volunteer, non-profit organization involved in development of international healthcare standards. HL7 is also used to refer to some of the specific standards created by the organization. HL7 and its members provide a framework and related standards for the exchange, integration, sharing, and retrieval of electronic health information.

In the example of FIG. 1 a medical image is created by scanner (104) in a hospital (102) and sent to the medical imaging cloud gateway (110) according to a protocol supported by the hospital (102). The medical images commonly range in size from 50 to 500 kilobytes, although the medical images may be larger and smaller. Each image is often called a slice and many slices together make a series of images that are processed together for medical treatment. A series may contain a single image or thousands of images. Examples of scanners useful in producing medical images according to embodiments of the present invention include magnetic resonance scanners, computed tomography scanners, digital radiography scanners and many others as will occur to those of skill in the art. Many manufacturers produce such scanners such as General Electric, Siemens, and others. The example of a scanner (104) in a hospital (102) is for explanation and not for limitation. In fact, medical images that may be administered according to embodiments of the present invention may be created in any health care setting such as clinics, MRI centers (106), doctor's offices (108) and many others as will occur to those of skill in the art.

The medical digital image communications protocol adapter (112) of FIG. 1 receives a request for an image processing transaction to process the medical digital image. The request is transmitted according to one of a plurality of a medical image communications protocol supported by medical digital image communications protocol adapter and used by a producer of the medical images. The request may be received according to any number of protocols supported by the provider of the digital image such as DICOM, HL7, and others as will occur to those of skill in the art. The request received in the medical digital image protocol adapter (112) contains a medical image to be processed, metadata describing the medical image, and an identification of the processing to be performed on the image.

An image processing transaction is request to perform one or more image processing workflows on one or more medical images in the medical imaging cloud computing environment. A workflow is typically implemented as one or more services that are reusable components of a data processing system. The services of the workflow are bound together and executed to carry out the workflow. Such workflows can include analytics for tumor detection, tumor growth, aneurysm detection, vessel separation in a patients head, and many other medical conditions, workflows for image compression, image resolution, distribution of images, and so on. Many other workflows for medical image processing will occur to those of skill in the art.

The medical digital image communications protocol adapter (112) of FIG. 1 parses the request according to the contents of the request and the structure of the request. The structure of the request may be defined by the protocol and standard in which the request was created. The medical digital image communications protocol adapter (112) of FIG. 1 may extract one or more the medical images associated with the request and also extract metadata describing the request and the medical images.

The medical digital image communications protocol adapter (112) of FIG. 1 creates a medical image business object representing the business transaction. A medical image business object is a data structure that represents the requested business transaction. The medical image business object includes metadata describing the request and the medical images processed in the requested transaction. The medical image business object has predefined structure. In some embodiments the medical image business object may be implemented as an XML file or other structured documents.

In the example of FIG. 1, the medical digital image communications protocol adapter (112) can create a medical image business object in dependence upon classification rules and the contents of the request. Classification rules are rules that are tailored to parsing the request according to the protocol and standard in which in which the request was created. The classification rules may be used to parse the request for the purpose of extracting medical images and metadata that are contained in the request. The classification rules are also tailored to develop the medical image business object by including the extracted images and metadata in a predefined structure in the medical image business object. Classification rules allow for disparate metadata, arriving in disparate protocols and standards, to be read, understood, classified, and organized according to a defined structure for the medical image business object.

In the example of FIG. 1, the medical image communications protocol adapter (112) sends the medical image business object to a medical digital image transaction cluster (120). The medical digital image transaction cluster (120) may be configured to store the medical image business object in a medical image metadata database. In the example of FIG. 1, the medical image metadata database may be embodied, for example, as a relational database configured to store and provide access to medical image metadata such as the medical image business object.

In the example of FIG. 1, the medical image communications protocol adapter (112) may store the medical images (114) locally in a medical image repository on the medical imaging gateway. Alternatively, the medical image communications protocol adapter (112) may send the medical images (114) to the medical digital image transaction cluster (120), which may store the images in a medical image repository (122) in the primary integrated delivery network (150). In the example of FIG. 1, the medical image repository (122) may be embodied as any form of persistent computer memory configured to receive and provide access to medical images.

The medical digital image transaction cluster (120) of FIG. 1 may select, in dependence upon workflow selection rules and the attributes of the medical image business object, one or more medical analytic workflows to process the medical image. Workflow selection rules are rules that are tailored to carrying out the image processing transaction on the medical images and the medical image business object according to the request received by the health care provider. The workflow selection rules can identify the necessary requirements of the transaction and select workflows having services that carry out those requirements. The workflow selection rules may also select workflows that are tailored for the attributes of medical images that are to be processed. Examples of such attributes include the slice size of a medical image, the number of slices that comprise the medical image, the type of scanner used to create the images, and so on. Workflows may include analytics for tumor detection, tumor growth, aneurysm detection, vessel separation in a patients head, and many other medical conditions. Workflows may also exist for image compression, image resolution, image distribution, and so on.

The medical digital image transaction cluster (120) of FIG. 1 process the medical image of the request with the medical analytic workflows, thereby creating a resultant business object (125) and resultant medical image (126). Processing the medical image is typically carried out by executing the selected medical analytic workflows and creating results for transmission to the health care provider. In the example of FIG. 1, the resultant medical image (126) may be a medical image that is produced by executing the one or more workflows using medical images contained in the request as input to the one or more workflows.

The medical digital image transaction cluster (120) of FIG. 1 routes, in dependence upon content routing rules and the attributes of the resultant business object, the resultant medical image (126) to one or more destinations. Examples of destinations in FIG. 1 include the hospital (102), the MRI center (106), the doctor's office (108), each of which may be in one or more networks for health care providers (154). The example destinations of FIG. 1 are for explanation and not for limitation. In fact, embodiments of the present invention may route the resultant medical image to many different destinations such as other hospitals, clinics, houses of doctors, patients, technicians, workstations, PDAs and many others as will occur to those of skill in the art.

In the example of FIG. 1, the resultant medical image (126) may be routed to one or more destinations in dependence upon content routing rules. In the example of FIG. 1, content routing rules are rules dictating the manner in which resultant medical images are routed to the destination. Such rules are often based on the content of the resultant medical image such that the image is routed to an appropriate health care provider in a manner that conforms to both security and privacy requirements. Often the destination of the image is a different location, logical or physical, from the provider of the original medical image prior to its being processed by the medical digital image transaction cluster. Content routing rules may also dictate the manner in which the health care provider may access the resultant medical images and who may access such images. Routing the resultant medical image to one or more destinations according to the example of FIG. 1 can include extracting metadata from the resultant business object, creating a response to the request the response conforming to a particular digital image communications protocol used for the destination, and transmitting the response according to the particular digital image communications protocol supported by the destination such as, for example, DICOM, HL7, and others as will occur to those of skill in the art.

Routing the resultant medical image to one or more destinations may also include sending a notification describing the resultant medical image to the destination. Examples of such a notification include an email message or a text message that is sent to a health care provider notifying the health care provider that the response to the request is ready for viewing. The notifications may also include information indicating that the workflows processing the medical images identified aspects of the images that are consistent with a medical condition such as tumor, aneurism, vessel separation, and so on.

The medical cloud computing environment (100) of FIG. 1 is not limited to administering medical images. The medical cloud computing environment (100) is also useful in managing failover operations according to embodiments of the present invention. The medical cloud computing environment of FIG. 1 includes a failover hold module (236). The failover hold module (236) of FIG. 1 is a module of computer program instructions that, when executed, controls the amount of errors that are generated in the medical cloud computing environment (100) when some component of data storage in the medical cloud computing environment (100) becomes unavailable. In the example of FIG. 1, components of data storage in the medical cloud computing environment (100) can include, for example, the medical image repository (116), computer memory that resides on individual machines within the medical digital image transaction cluster (120), the metadata database (124), medical image repository (122), as well as other forms of data storage that will occur to those of skill in the art.

In the example of FIG. 1, the failover hold module (236) may manage failover operations by identifying a data storage access failure. A data storage access failure may include, for example, a failed attempt to write to data storage in the medical cloud computing environment (100), a failed attempt to read from data storage in the medical cloud computing environment (100), and so on. In the example of FIG. 1, the failover hold module (236) may identify a data storage access failure, for example, by receiving a message from an entity that attempted to access data storage indicating that the attempt failed, by examining error logs in the medical cloud computing environment (100), and so on.

In the example of FIG. 1, the failover hold module (236) may further manage failover operations by preventing the execution of all read operations received after the data storage access failure was identified. In the example of FIG. 1, preventing the execution of all read operations received after the data storage access failure was identified may be carried out by delaying the dispatch of the read operations. For example, if an attempted access of a particular component of data storage resulted in the generation of an access failure, all subsequent read operations directed to the particular component of data storage should not be dispatched for execution until a point in time at which failover hold module (236) has verified that the particular component of data storage is accessible. In such a way, the failover hold module (236) may 'hold' all of the read requests until a point in time at which dispatching the read requests should not result in an access failure.

In the example of FIG. 1, the failover hold module (236) may further manage failover operations by executing all write operations received after the data storage access failure was identified, including writing data to cache (237). In the example of FIG. 1, the cache (237) represents a component of data storage that is distinct from the component of data storage that was the subject of the data storage access failure. In such an example, rather than attempting to execute a write operation to the component of data storage that was the subject of the data storage access failure, the failover hold module (236) may instead execute the write operations to the cache (237) so that the write operation will execute without error.

In the example of FIG. 1, the failover hold module (236) may further manage failover operations by identifying that a failover to alternative data storage is complete. In the example of FIG. 1, a failover to alternative data storage is complete when the alternative data storage is used in place of the data storage that was the subject of the data storage access failure. A failover to alternative data storage may be carried out, for example, by physically replacing the data storage with alternative data storage, by updating a page table such that a virtual address that pointed to the data storage now points to the alternative data storage, and in other ways as will occur to those of skill in the art. In the example of FIG. 1, a failover to alternative data storage can also include replicating the contents of the data storage within the alternative data storage, so that the alternative data storage has the same content in the same locations as the data storage.

In the example of FIG. 1, the failover hold module (236) may further manage failover operations by copying, from cache (237) to the alternative data storage, the data written to the cache (237) as part of the write operations. In the example of FIG. 1, data was written to cache (237) in lieu of writing data to data storage in response to the receipt of write operations directed to the data storage that were received after the failure to access data storage was identified. Such data may be written to cache (237) without reporting an error. In the example of FIG. 1, because a failover to alternative data storage has been completed, data that was originally intended for data storage but instead written to cache may be copied from cache (237) to the alternative data storage. In such a way, write operations that would have resulted in errors if an attempt was made to write data to data storage can instead be written to cache (237) and subsequently copied to the alternative data storage after failover to the alternative data storage has occurred, such that the alternative data storage has the same contents that the data storage would have contained if not for the access failure.

In the example of FIG. 1, the failover hold module (236) may further manage failover operations by executing the held read operations, including reading data from the alternative data storage. In the example of FIG. 1, all read operations directed to the data storage that were received after the failure to access data storage was identified were prevented from executing. After failover to alternative data storage has occurred, such read operations may be executed by directing the read operations to the alternative data storage. The read operations may be executed by directing the read operations to the alternative data storage because a failover to alternative data storage has been completed, and as such, the alternative data storage may be accessed as if it were the original data storage that could not be accessed. In such a way, read operations that would have resulted in errors can be delayed and subsequently executed after failover to the alternative data storage has occurred, thereby enabling the read operations to be carried out.

The medical cloud computing environment (100) of FIG. 1 is not limited to administering medical images and managing failover operations. The medical cloud computing environment (100) of FIG. 1 is also useful in managing maintenance of a cluster of computers according to embodiments of the present invention. The failover hold module (236) may manage failover operations by identifying one or more scheduled maintenance operations to be executed on a cluster of computers such as the medical digital image transaction cluster (120). In the example of FIG. 1, the one or more scheduled maintenance operations are operations designed to keep the cluster of computers operating at expected performance levels. Examples of scheduled maintenance operations include, for example, backing up data storage, performing software updates, executing anti-virus software, and so on.

The failover hold module (236) may further manage failover operations by initiating the execution of the scheduled maintenance operations. Initiating the execution of the scheduled maintenance operations may be carried out, for example, by executing a software module that carries out maintenance operations. For example, a software module that performs a data backup may be executed to initiate data backup maintenance operations, a software module that performs an operating system update may be executed to initiate system update maintenance operations, and so on.

The failover hold module (236) may further manage failover operations by preventing the execution of all data storage access requests that were received after initiating the execution of the scheduled maintenance operations. In the example of FIG. 1, preventing the execution of all data storage access requests that were received after initiating the execution of the scheduled maintenance operations may be carried out by delaying the dispatch of the data storage access requests for execution. For example, if data storage was being backed up to off-site memory, executing a data storage access request may result in data storage being altered such that the backup of the data storage is out-of-date before the backup has even completed. As such, the failover hold module may 'hold' all of the data storage access requests until a point in time at which the backup of data storage has completed.

In the example method of FIG. 1, preventing the execution of all data storage access requests that were received after initiating the execution of the scheduled maintenance operations can include storing, in a cache (237), all data storage access requests that were received after initiating the execution of the scheduled maintenance operations. In the example of FIG. 1, the cache (237) represents a component of data storage that is distinct from the data storage that the data storage access request was directed to. In such an example, rather than attempting to execute an access of the data storage of a system that is executing maintenance operations, the failover hold module (236) may instead store all data storage access requests that were received after initiating the execution of the scheduled maintenance operations in the cache (237) so that the data storage access requests may be executed upon the completion of the maintenance operations.

The failover hold module (236) may further manage failover operations by determining that the scheduled maintenance operations are complete. In the example of FIG. 1, determining that the scheduled maintenance operations are complete may be carried out, for example, by receiving a notification indicating that the scheduled maintenance operations, by the expiration of a predetermined time period since the scheduled maintenance operations began, by identifying the processes executing on a particular computer in the cluster of computers and determining that the all processes that are part of the scheduled maintenance operations are no longer executing, and in other ways as will occur to those of skill in the art.

The failover hold module (236) may further manage failover operations by executing all data storage access requests that were received after initiating the execution of the scheduled maintenance operations. In the example of FIG. 1, executing all data storage access requests that were received after initiating the execution of the scheduled maintenance operations may be carried out, for example, by retrieving the data storage access requests that were received after initiating the execution of the scheduled maintenance operations from the cache (237). In such an example, executing all data storage access requests that were received after initiating the execution of the scheduled maintenance operations may further be carried out by dispatching such data storage access requests for execution after the data storage access requests have been retrieved from the cache (237).

The arrangement of servers and other devices making up the exemplary system illustrated in FIG. 1 are for explanation, not for limitation. Data processing systems useful according to various embodiments of the present invention may include additional servers, routers, other devices, peer-to-peer architectures, databases containing other information, not shown in FIG. 1, as will occur to those of skill in the art. Networks in such data processing systems may support many data communications protocols, including for example Transmission Control Protocol ('TCP'), Internet Protocol ('IP'), HyperText Transfer Protocol ('HTTP'), Wireless Access Protocol ('WAP'), Handheld Device Transport Protocol ('HDTP'), and others as will occur to those of skill in the art. Various embodiments of the present invention may be implemented on a variety of hardware platforms in addition to those illustrated in FIG. 1.

Figure 2:
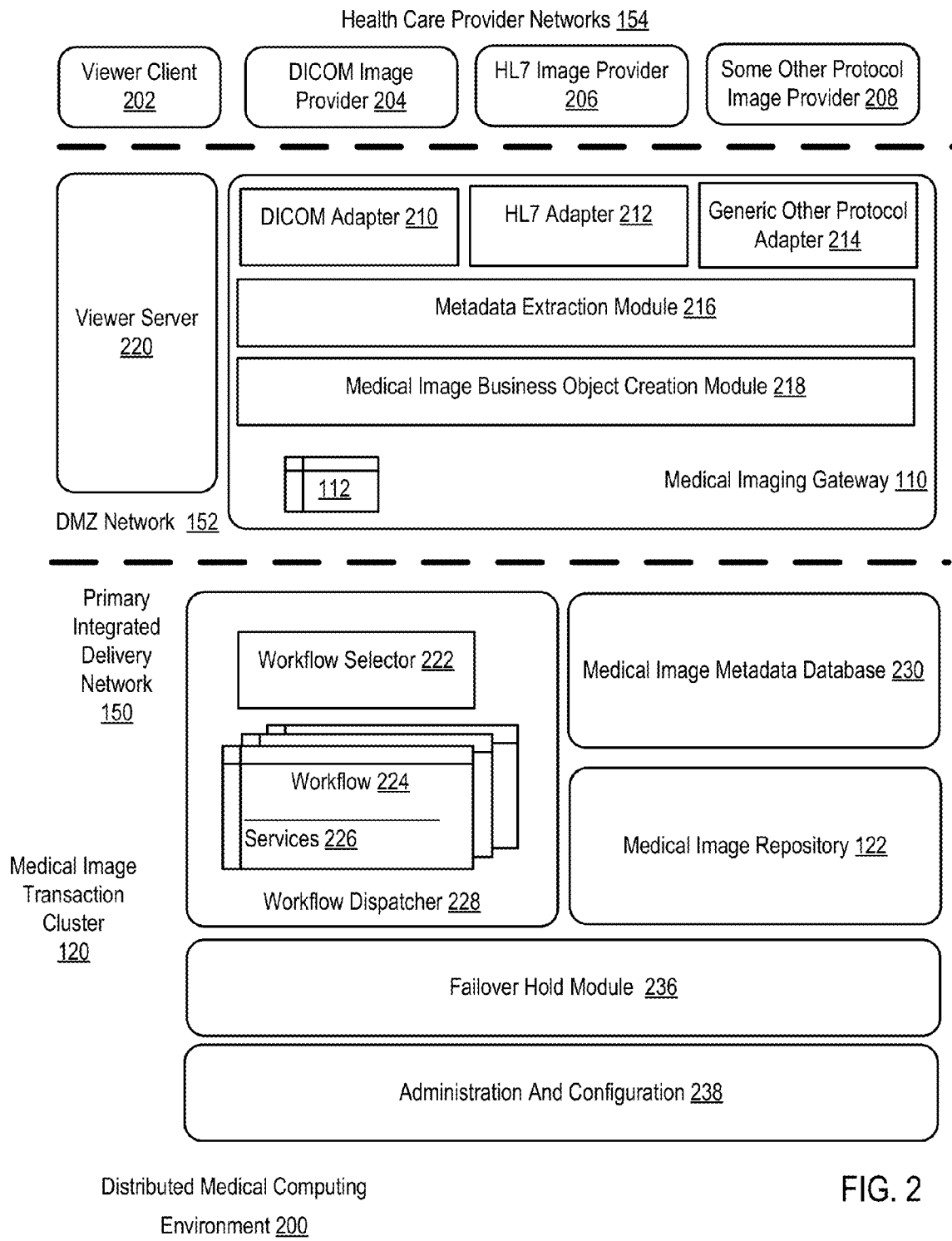
FIG. 2 sets forth an example system for administering medical digital images and managing failover operations in a distributed medical computing environment.

For further explanation, FIG. 2 sets forth an example system for administering medical digital images and managing failover operations in a distributed medical computing environment (200). The medical computing environment of FIG. 2 includes two networks, a DMZ network (152) and a primary integrated delivery network (105). The distributed medical computing environment (200) administers medical digital images for a number of health care providers who provide medical images and receives the results of imaging transactions processed on those medical images, and also dynamically allocates business workflows, according to embodiments of the present invention. The distributed medical computing environment may be implemented as a cloud computing environment that is accessible to the health care providers through the health care provider networks (154).

The example distributed medical image computing environment (200) of FIG. 2 includes a medical gateway (110), a module of automated computing machinery that includes a DICOM adapter (210), an HL7 adapter (212), generic other protocol adapter, a metadata extraction module (216) and a medical image business object creation module (218). The medical imaging gateway (110) of FIG. 2 receives, in one of the medical digital image communications protocol adapter (210, 212, 214), a request for an image processing transaction to process the medical digital image. The request contains a medical image to be processed, metadata describing the medical image, and an identification of the processing to be performed on the image.

The request is transmitted according to one of a plurality of a medical image communications protocol supported by medical digital image communications protocol adapter and used by a producer of the medical images. For example, the medical imaging gateway (110) of FIG. 2 is capable of receiving a request for an image processing transaction from a health care provider (204) according to the DICOM standard, the HL7 standard, and other protocols and standards for creating and transmitted medical digital images. In the example of FIG. 2, the DICOM adapter (210) is capable of receiving and parsing the request according to the DICOM standard, the HL7 Adapter (212) is capable of receiving and parsing the request according the HL7 standard, and the generic other protocol adapter (214) is capable of receiving and parsing the request according to some other protocol that will occur to those of skill in the art.

The metadata extraction module (216) of FIG. 2 extracts the metadata from the parsed request according to the standards and protocol used to create and transmit the request. The metadata extraction module (216) of FIG. 2 may also be configured to provide the extracted metadata to the medical image business object creation module. The medical image business object creation module in turn creates, in dependence upon classification rules and the contents of the request, a medical image business object (112) representing the business transaction. The medical image business object includes a predefined structure and may be implemented as a structured document such as an XML document.

The medical imaging gateway (110) of FIG. 2 sends the medical image business object (112) to a medical image transaction cluster (120) in the primary integrated delivery network. The medical image transaction cluster (120) includes a workflow dispatcher (228), a medical image metadata database (230), a medical image repository (122), a security module (232), and a medical imaging cloud computing administration and configuration module (238). The workflow dispatcher (228) can receive the medical image business object and store the medical image business object (112) in the medical image metadata database (230). The workflow dispatcher (228) can also receive medical images and store the medical image in the medical image repository (122).

The workflow dispatcher (228) of FIG. 2 may also include a workflow selector (222) that selects, in dependence upon workflow selection rules and the attributes of the medical image business object, one or more medical analytic workflows to process the medical image. As described above, workflow selection rules are rules that are tailored to carrying out the image processing transaction on the medical images and the medical image business object according to the request received by the health care provider. The workflow selection rules can identify the necessary requirements of the transaction and select workflows having services that carry out those requirements. The workflow selection rules may also select workflows that are tailored for the attributes of medical images that are to be processed.

The workflow dispatcher (228) of FIG. 2 may also process the medical image of the request with the medical analytic workflows, thereby creating a resultant business object and resultant medical image. Processing the medical image is typically carried out by executing the selected medical analytic workflows and creating results for transmission to the health care provider. In the example of FIG. 2, the resultant medical image may be a medical image that is produced by executing the one or more workflows using medical images contained in the request as input to the one or more workflows.

The workflow dispatcher (228) may also route, in dependence upon content routing rules and the attributes of the resultant business object, the resultant medical image to one or more destinations. The workflow dispatcher (228) of FIG. 2 routes the resultant medical image to one or more destinations by extracting metadata from the resultant business object, creating a response to the request the response conforming to a particular digital image communications protocol used for the destination, and transmitting the response according to the particular digital image communications protocol. The workflow dispatcher (228) of FIG. 2 may route the resultant medical image to one or more destinations by storing the resultant medical image on the medical imaging gateway (110) assigned to the destination of the medical image. The workflow dispatcher may then transmit in the response data access information to access the resultant medical image on the gateway. A health care provider may then view the resultant medical images using the viewer server (220) in the DMZ network (152) through the use of a viewer client (202) at the health care provider's location.

The distributed medical computing environment (200) is also capable of managing failover operations according to embodiments of the present invention. The example of FIG. 2 includes a failover hold module (236). The failover hold module (236) of FIG. 2 is a module of computer program instructions that, when executed, controls the amount of errors that are generated in the medical cloud computing environment when some component of data storage in the medical cloud computing environment becomes unavailable. In the example of FIG. 2, components of data storage in the medical cloud computing environment can include, for example, a medical image repository, computer memory that resides on individual machines within the medical digital image computing environment, a metadata database, a medical image repository, as well as other forms of data storage that will occur to those of skill in the art.

In the example of FIG. 2, the failover hold module (236) may manage failover operations by identifying a data storage access failure. A data storage access failure may include, for example, a failed attempt to write to data storage in the medical cloud computing environment, a failed attempt to read from data storage in the medical cloud computing environment, and so on. In the example of FIG. 2, the failover hold module (236) may identify a data storage access failure, for example, by receiving a message from an entity that attempted to access data storage indicating that the attempt failed, by examining error logs in the medical cloud computing environment, and so on.

In the example of FIG. 2, the failover hold module (236) may further manage failover operations by preventing the execution of all read operations received after the data storage access failure was identified. In the example of FIG. 2, preventing the execution of all read operations received after the data storage access failure was identified may be carried out by delaying the dispatch of the read operations. For example, if an attempted access of a particular component of data storage resulted in the generation of an access failure, all subsequent read operations directed to the particular component of data storage should not be dispatched for execution until a point in time at which failover hold module (236) has verified that the particular component of data storage is accessible. In such a way, the failover hold module (236) may 'hold' all of the read requests until a point in time at which dispatching the read requests should not result in an access failure.

In the example of FIG. 2, the failover hold module (236) may further manage failover operations by executing all write operations received after the data storage access failure was identified, including writing data to cache. In the example of FIG. 2, the cache represents a component of data storage that is distinct from the component of data storage that was the subject of the data storage access failure. In such an example, rather than attempting to execute a write operation to the component of data storage that was the subject of the data storage access failure, the failover hold module (236) may instead execute the write operations to the cache so that the write operation will execute without error.

In the example of FIG. 2, the failover hold module (236) may further manage failover operations by identifying that a failover to alternative data storage is complete. In the example of FIG. 2, a failover to alternative data storage is complete when the alternative data storage is used in place of the data storage that was the subject of the data storage access failure. A failover to alternative data storage may be carried out, for example, by physically replacing the data storage with alternative data storage, by updating a page table such that a virtual address that pointed to the data storage now points to the alternative data storage, and in other ways as will occur to those of skill in the art. In the example of FIG. 2, a failover to alternative data storage can also include replicating the contents of the data storage within the alternative data storage, so that the alternative data storage has the same content in the same locations as the data storage.

In the example of FIG. 2, the failover hold module (236) may further manage failover operations by copying, from cache to the alternative data storage, the data written to the cache as part of the write operations. In the example of FIG. 2, data was written to cache in lieu of writing data to data storage in response to the receipt of write operations directed to the data storage that were received after the failure to access data storage was identified. Such data may be written to cache without reporting an error. In the example of FIG. 2, because a failover to alternative data storage has been completed, data that was originally intended for data storage but instead written to cache may be copied from cache to the alternative data storage. In such a way, write operations that would have resulted in errors if an attempt was made to write data to data storage can instead be written to cache and subsequently copied to the alternative data storage after failover to the alternative data storage has occurred, such that the alternative data storage has the same contents that the data storage would have contained if not for the access failure.

In the example of FIG. 2, the failover hold module (236) may further manage failover operations by executing the held read operations, including reading data from the alternative data storage. In the example of FIG. 2, all read operations directed to the data storage that were received after the failure to access data storage was identified were prevented from executing. After failover to alternative data storage has occurred, such read operations may be executed by directing the read operations to the alternative data storage. The read operations may be executed by directing the read operations to the alternative data storage because a failover to alternative data storage has been completed, and as such, the alternative data storage may be accessed as if it were the original data storage that could not be accessed. In such a way, read operations that would have resulted in errors can be delayed and subsequently executed after failover to the alternative data storage has occurred, thereby enabling the read operations to be carried out.

For further explanation, FIG. 3 sets forth a block diagram of an example medical image business object (118) according to embodiments of the present invention. The medical image business object (118) of FIG. 3 includes a request ID (302). In the example of FIG. 3, the request ID (302) can include an identification of the particular request for a medical image processing transaction. The medical image business object (118) of FIG. 3 includes a request type (304). The request type (304) of FIG. 3 can identify the kind of image processing transaction being requested.

The medical image business object (118) of FIG. 3 also includes an action ID (306). The action ID (306) of FIG. 3 can identify a particular action or workflow to be executed in the image processing transaction. The medical image business object (118) of FIG. 3 also includes a provider ID (308) identifying the provider of the medical images to be processed in the image transaction. The medical image business object (118) of FIG. 3 further includes image provider protocol (338) that identifies the protocol and standard in which the images and request were created such as DICOM, HL7, and so on as will occur to those of skill in the art.

The medical image business object (118) of FIG. 3 includes a patient ID (310) that identifies the patient. An identification of the patient may include a name, social security number or other unique identification of the patient. The medical image business object (118) of FIG. 3 also includes a physician ID (312) identifying a physician associated with the patient and a technician ID (314) identifying one or more technician that performed the scan to create the medical images associated with the request.

The medical image business object (118) of FIG. 3 includes a scanner ID (316) identifying the scanner used to produce the medical images associated with the request. The identification of the scanner can include a manufacturer name, serial number of the scanner or any other identification that will occur to those of skill in the art. The medical image business object (118) of FIG. 3 also includes a scanner type (318) identifying the type of scanner such as magnetic resonance scanners, computer tomography scanners, digital radiography scanners and so forth as will occur to those of skill in the art.

The medical image business object (118) of FIG. 3 includes an image ID (320) identifying the medical image. The image ID (320) may also identify the image and the series of images that the image is a part of. The medical image business object (118) of FIG. 3 also includes an image type (322) that identifies the type of image. The type of image may also identify the type of images in a series of images.

The medical image business object (118) of FIG. 3 also includes a patient location (324) and a destination location (326). In the example of FIG. 3, the patient location (324) can identify the location of the patient and the destination location (326) can identify the location to which the processed resultant medical images and associated notifications are to be sent.

The medical image business object (118) of FIG. 3 also includes a receiving gateway ID (328). The receiving gateway ID (328) can identify the medical imaging gateway in the medical imaging cloud computing environment in which the request for the imaging transaction was received. The medical image business object (118) of FIG. 3 also includes a destination gateway ID (330). The destination gateway ID (330) can identify the medical imaging gateway in the medical imaging cloud computing environment to which a response to a request, the resultant processed images, and any notifications are to be sent.

The medical image business object (118) of FIG. 3 includes an original image pointer (332) that points to the original images or series of images in data storage in the medical imaging cloud computing environment. In some embodiments, the original images may be stored on the medical imaging gateway that received the request for the transaction. The medical image business object (118) of FIG. 3 includes an interim image pointer (334) that points to the current state of an image or series of images during the execution of the imaging transaction. Such images may be interim in the sense that some of the workflows for the images have been executed but the image transaction is not complete. The medical image business object (118) of FIG. 3 includes a resultant image pointer (336) that points to the resultant image after completion of the image transaction. The fields and structure of the medical image business object (118) of FIG. 3 are for explanation and not for limitation. Business objects, interim business objects, and the like useful in embodiments of the present invention may include many different fields and different structure as will occur to those of skill in the art.

Figure 4:
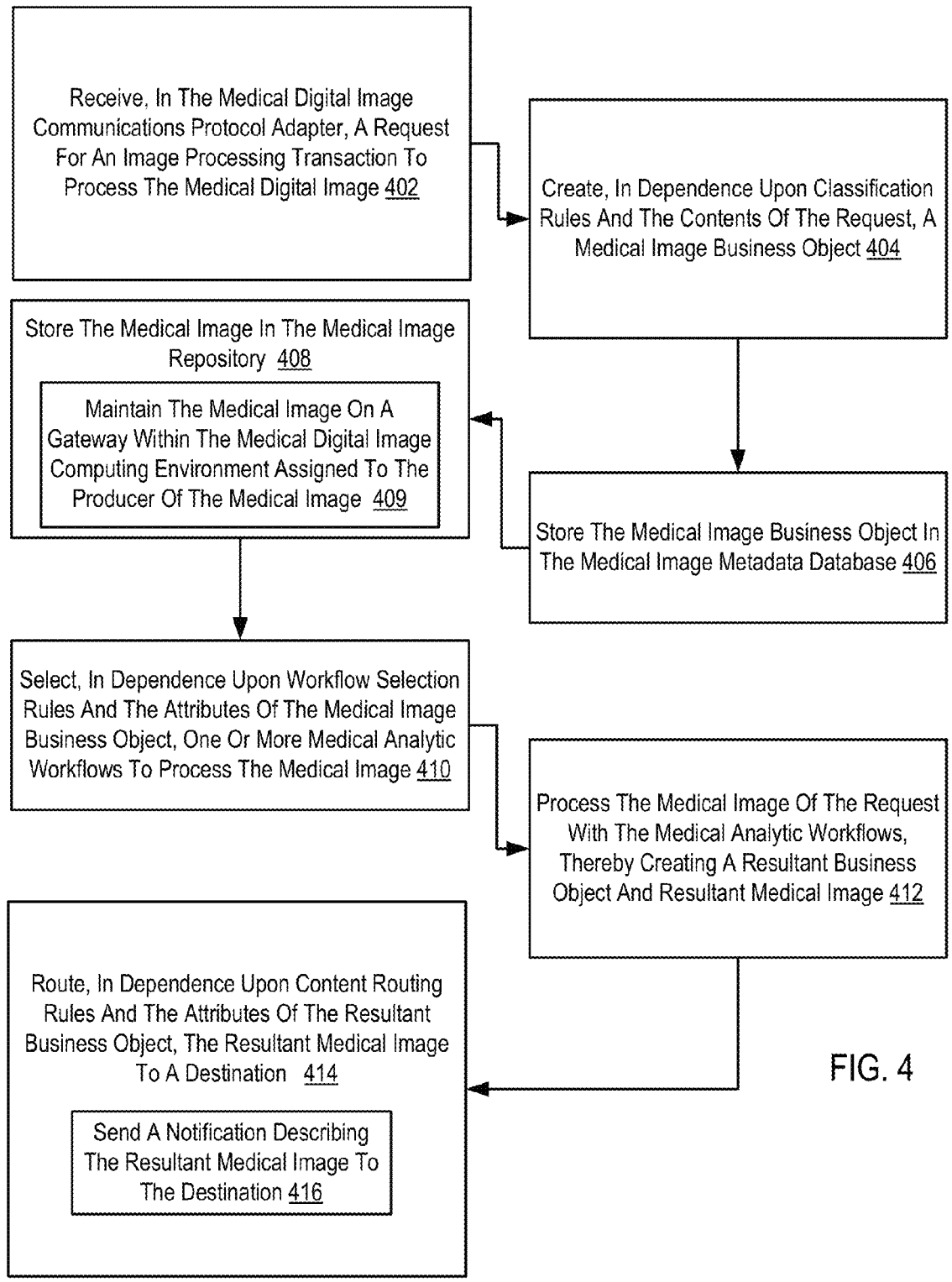
FIG. 4 sets forth a flow chart illustrating an example method of administering medical digital images in a distributed medical digital image computing environment according to embodiments of the present invention.

For further explanation, FIG. 4 sets forth a flow chart illustrating an example method of administering medical digital images in a distributed medical digital image computing environment according to embodiments of the present invention. In some embodiments, the distributed medical digital image computing environment is implemented as a cloud computing environment. The medical digital image computing environment may include a medical digital image communications protocol adapter, a medical image metadata database, a medical image repository, and a medical image transaction workflow dispatcher.

The method of FIG. 4 includes receiving (402), in the medical digital image communications protocol adapter, a request for an image processing transaction to process one or more of the medical digital images. In the example of FIG. 4, the request may include a medical image to be processed and metadata describing the medical image. The metadata describing the medical image may include, for example, an identification of the image type, a specification of the image resolution, a specification of the image size, and so on. In the example of FIG. 4, the request may also include an identification of the processing to be performed on the image. The identification of the processing to be performed on the image may include, for example, an identification of a workflow that is to process the image. In the example of FIG. 4, the request may be transmitted according to one of a plurality of a medical image communications protocol supported by medical digital image communications protocol adapter and used by a producer of the medical images.

The method of FIG. 4 includes creating (404) a medical image business object. In the example of FIG. 4, the medical image business object may represent an image processing operation that is to be performed. The medical image business object may include, for example, an identification of one or more workflows that will carry out the image processing operation that is to be performed, an identification of a destination that is to receive the output generated by performing the image processing operation, a description of the data types for inputs and outputs for the one or more workflows that will carry out the image processing operation, and so on.

In the example method of FIG. 4, creating (404) a medical image business object may be carried out in dependence upon classification rules and the contents of the request. Classification rules are rules that may be tailored to parsing and identifying the type of request according to the protocol and standard in which in which the request was created. The classification rules may also be tailored to develop the medical image business object by including the extracted images and metadata in a predefined structure in the medical image business object. Classification rules allow for disparate metadata, arriving in disparate protocols and standards to be read, understood classified and organized according to a defined structure for the medical image business object. Creating (404) the medical image business object may be carried out by extracting from the request metadata describing the image according to the medical image communications protocol of the request and conforming the metadata to the predefined structure of the medical image business object.

The method of FIG. 4 also includes storing (406) the medical image business object in the medical image metadata database. In the example method of FIG. 4, storing (406) the medical image business object in the medical image metadata database may include storing the medical image business object locally on a medical imaging gateway. Alternatively, storing (406) the medical image business object in the medical image metadata database may include providing the business object for storage elsewhere in the distributed processing system.

The method of FIG. 4 also includes storing (408) the medical image in the medical image repository. In the example of FIG. 4, storing (408) the medical image in the medical image repository may include maintaining (409) the medical image on a gateway within the medical digital image computing environment. Such a gateway may be assigned to the producer of the medical image, such that all medical images produced by a particular producer of medical images are stored in a single, identifiable gateway. Particular gateways may be assigned to particular producers, for example, based on the type of images produced by the producer, based on the size of images produced by the producer, and in other ways as will occur to those of skill in the art.

The method of FIG. 4 also includes selecting (410), in dependence upon workflow selection rules and the attributes of the medical image business object, one or more medical analytic workflows to process the medical image. Workflow selection rules are rules that are tailored to carrying out the image processing transaction on the medical images and the medical image business object according to the request received by the health care provider. Such workflow selection rules identify the necessary requirements of the transaction and select workflows having services that carry out those requirements as well as select workflows that are tailored for the attributes of those images such as the slice size, number of slices, type of scanner used to create the images, standards used for the images and many others as will occur to those of skill in the art. Workflows may include analytics for tumor detection, tumor growth, aneurysm detection, vessel separation in a patients head, and many other medical conditions, workflows for image compression, image resolution, distribution of images, and many other workflows for medical image processing that will occur to those of skill in the art.

The method of FIG. 4 also includes processing (412) the medical image of the request with the medical analytic workflows, thereby creating a resultant business object and resultant medical image. Processing (412) the medical image of the request with the medical analytic workflows may be carried out, for example, by executing the selected workflows using the medical images and the medical image business model associated with the requested image processing transaction as inputs to the selected workflows.

The method of FIG. 4 also includes routing (414), in dependence upon content routing rules and the attributes of the resultant business object, the resultant medical image to one or more destinations. Content routing rules are rules dictating the manner in which resultant medical images are routed to the destination. Such rules are often based on the content of the resultant medical image such that the image is routed to an appropriate health care provider in a manner that conforms to both security and privacy. Often the destination of the image is a different location, logical or physical, from the provider of the original medical image prior to its being processed by the medical digital image transaction cluster. Content routing rules may also dictate the manner in which the health care provider may access the resultant medical images and who may access such images.

Routing (414) the resultant medical image according to the method of FIG. 4 may include extracting metadata from the resultant business object, creating a response to the request the response conforming to a particular digital image communications protocol used for the destination, and transmitting the response according to the particular digital image communications protocol. Routing (414) the resultant medical image to one or more destinations may also include storing the resultant medical image on a gateway within the medical digital image computing environment assigned to the producer of the medical image and transmitting the response according to the particular digital image communications protocol further comprises transmitting in the response data access information to access the resultant medical image on the gateway.

Routing (414), in dependence upon content routing rules and the attributes of the resultant business object, the resultant medical image to one or more destinations according to the method of FIG. 4 also includes sending (414) a notification describing the resultant medical image to the one or more destinations. Examples of a such a notification may be an email message or a text message to a health care provider notifying the health care provider that the response to the request is ready for viewing or that the workflows processing the medical images identified aspects of the images that are consistent with a medical condition such as tumor, aneurism, vessel separation, and so on as will occur to those of skill in the art.

Figure 5:
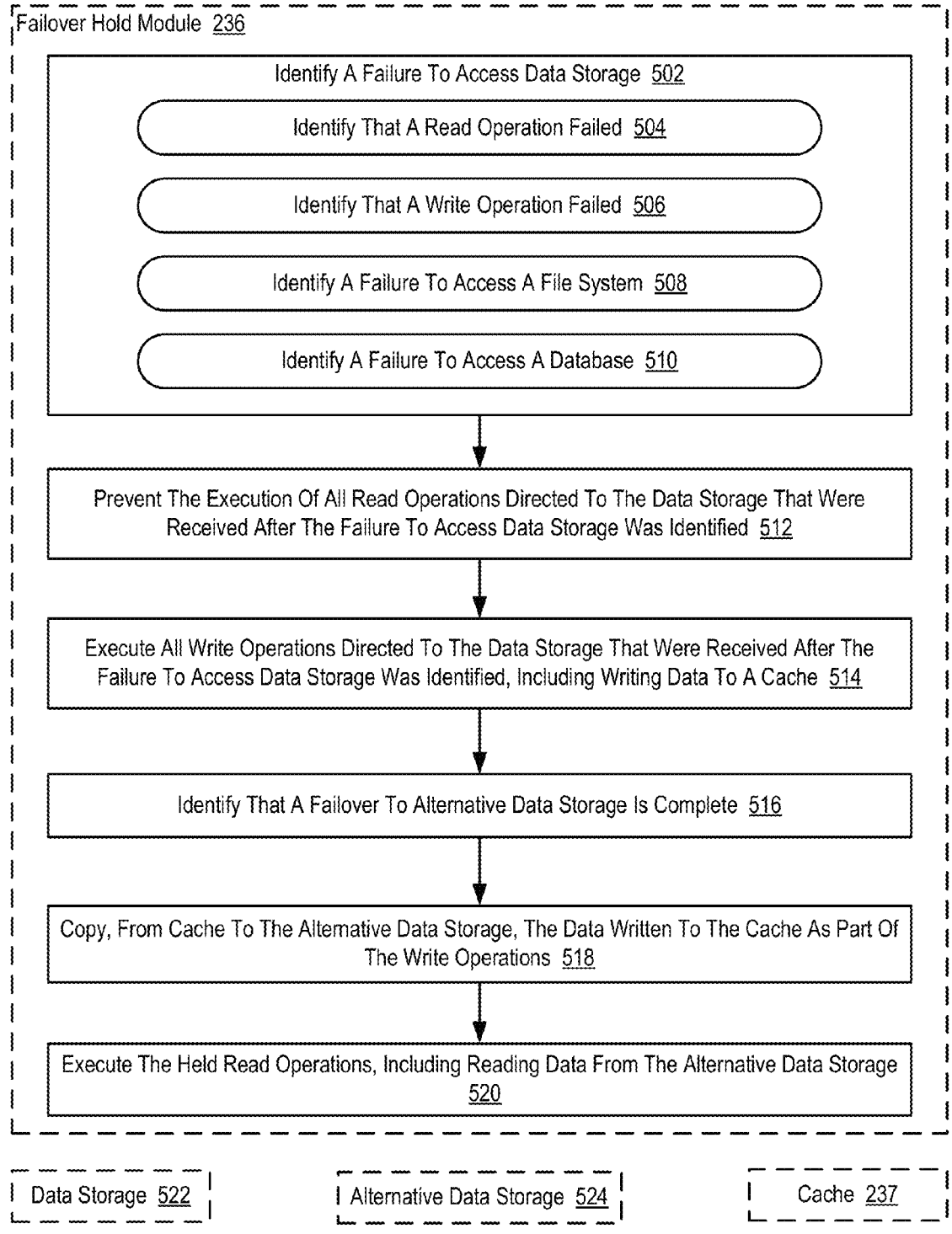
FIG. 5 sets forth a flow chart illustrating an example method of managing failover operations on a cluster of computers according to embodiments of the present invention.

For further explanation, FIG. 5 sets forth a flow chart illustrating an example method of managing failover operations on a cluster of computers according to embodiments of the present invention. The example method of FIG. 5 includes identifying (502), by a failover hold module (236), a failure to access data storage (522) in a cluster of computers. The failover hold module (236) of FIG. 5 is a module of computer program instructions that, when executed, controls the amount of errors that are generated in a medical cloud computing environment when data storage (522) in the medical cloud computing environment becomes unavailable. In the example of FIG. 5, the data storage (522) may be embodied as, for example, a file system, a database, computer memory that resides on individual machines within the cluster of computers, as well as other forms of data storage that will occur to those of skill in the art.

In the example of FIG. 5, the failover hold module (236) may identify (502) a failure to access data storage (522). A failure to access data storage (522) may include, for example, a failed attempt to write to data storage (522), a failed attempt to read from data storage (522), and so on. The failover hold module (236) may identify a failure to access data storage (522), for example, by receiving a message from an entity that attempted to access data storage (522) indicating that the attempt failed, by examining error logs in the medical cloud computing environment, and so on.

In the example method of FIG. 5, identifying (502) a failure to access data storage (522) can include identifying (504) that a read operation failed. Such a read operation represents an attempt to read data stored in a specified location of the data storage (522). The specified location of the data storage (522) may be embodied, for example, as a virtual address, a real address, a record number, and in other ways as will occur to those of skill in the art.

In the example method of FIG. 5, identifying (502) a failure to access data storage (522) can include identifying (506) that a write operation failed. Such a write operation represents an attempt to write data to a particular location in data storage (522). The particular location in data storage (522) may be embodied, for example, as a virtual address, a real address, a value that is otherwise used to organize data in data storage (522), and in other ways as will occur to those of skill in the art.

In the example method of FIG. 5, identifying (502) a failure to access data storage (522) can include identifying (508) a failure to access a file system. In the example of FIG. 5, a file system is used on data storage devices such as magnetic storage disks or optical discs to maintain the physical location of computer files. A file system may provide access to data on a file server by acting as clients for a network protocol such as the Network File System ('NFS') protocol. Alternatively, a file system may be a virtual file system and may exist only as an access method for virtual data.

In the example method of FIG. 5, identifying (502) a failure to access data storage (522) can include identifying (510) a failure to access a database. In the example of FIG. 5, a database is an organized collection of data that can be presented to users through various views and can be logically organized within data storage (522). In the example of FIG. 5, identifying (510) a failure to access a database can be carried out, for example, by determining that the data storage (522) upon which the database resides is unreachable. In the example of FIG. 5, however, identifying (510) a failure to access a database is distinct from a situation in which a database is accessible but no record associated with specified search criteria is included in the accessible database.

The example method of FIG. 5 also includes, without (512) reporting an error, preventing the execution of all read operations directed to the data storage (522) that were received after the failure to access data storage (522) was identified. In the example of FIG. 5, preventing the execution of all read operations directed to the data storage (522) that were received after the failure to access data storage (522) was identified may be carried out by delaying the dispatch of the read operations for execution. For example, if an attempted access of data storage (522) resulted in the generation of an access failure, all subsequent read operations directed to the data storage (522) should not be dispatched for execution until a point in time at which failover hold module (236) has verified that the data storage (526) is accessible. In such a way, the failover hold module (236) may 'hold' all of the read requests until a point in time at which dispatching the read requests should not result in an access failure.

The example method of FIG. 5 also includes, without (514) reporting an error, executing all write operations directed to the data storage (522) that were received after the failure to access data storage (522) was identified, including writing data to a cache (237). In the example of FIG. 5, the cache (237) represents a component of data storage that is distinct from the data storage (522) that was the subject of the data storage access failure. In such an example, rather than attempting to execute a write operation to the data storage (522) that was the subject of the data storage access failure, the failover hold module (236) may instead execute the write operations to the cache (237) so that the write operation will execute without error.

The example method of FIG. 5 also includes identifying (516) that a failover to alternative data storage (524) is complete. In the example of FIG. 5, a failover to alternative data storage (524) is complete when the alternative data storage (524) is used in place of the data storage (522) that was the subject of the data storage access failure. A failover to alternative data storage (524) may be carried out, for example, by physically replacing the data storage (522) with alternative data storage (524), by updating a page table such that a virtual address that pointed to the data storage (522) now points to the alternative data storage (524), and in other ways as will occur to those of skill in the art. In the example method of FIG. 5, a failover to alternative data storage (524) can also include replicating the contents of the data storage (522) within the alternative data storage (524), so that the alternative data storage (524) has the same content in the same locations as the data storage (522).

The example method of FIG. 5 also includes copying (518), from cache (237) to the alternative data storage (524), the data written to the cache (237) as part of the write operations. In the example of FIG. 5, data was written to cache (237) in lieu of writing data to data storage (522) in response to the receipt of write operations directed to the data storage (522) that were received after the failure to access data storage (522) was identified. Such data was written to cache (237) without (514) reporting an error. In the example of FIG. 5, because a failover to alternative data storage (524) has been completed, data that was originally intended for data storage (522) but instead written to cache (237) may be copied (518) from cache (237) to the alternative data storage (524). In such a way, write operations that would have resulted in errors if an attempt was made to write data to data storage (522) can instead be written to cache (237) and subsequently copied (518) to the alternative data storage (524) after failover to the alternative data storage (524) has occurred, such that the alternative data storage (524) has the same contents that the data storage (522) would have contained if not for the access failure.

The example method of FIG. 5 also includes executing (520) all held read operations that were directed to the data storage (522), including reading data from the alternative data storage (524). In the example of FIG. 5, all read operations directed to the data storage (522) that were received after the failure to access data storage (522) was identified were prevented from executing without (512) reporting an error. After failover to alternative data storage (524) has occurred, such read operations may be executed (520) by directing the read operations to the alternative data storage (524). The read operations may be executed (520) by directing the read operations to the alternative data storage (524) because a failover to alternative data storage (524) has been completed, and as such, the alternative data storage (524) may be accessed as if it were the original data storage (522) that could not be accessed. In such a way, read operations that would have resulted in errors can be delayed and subsequently executed after failover to the alternative data storage (524) has occurred, thereby enabling the read operations to be carried out.

Figure 6:
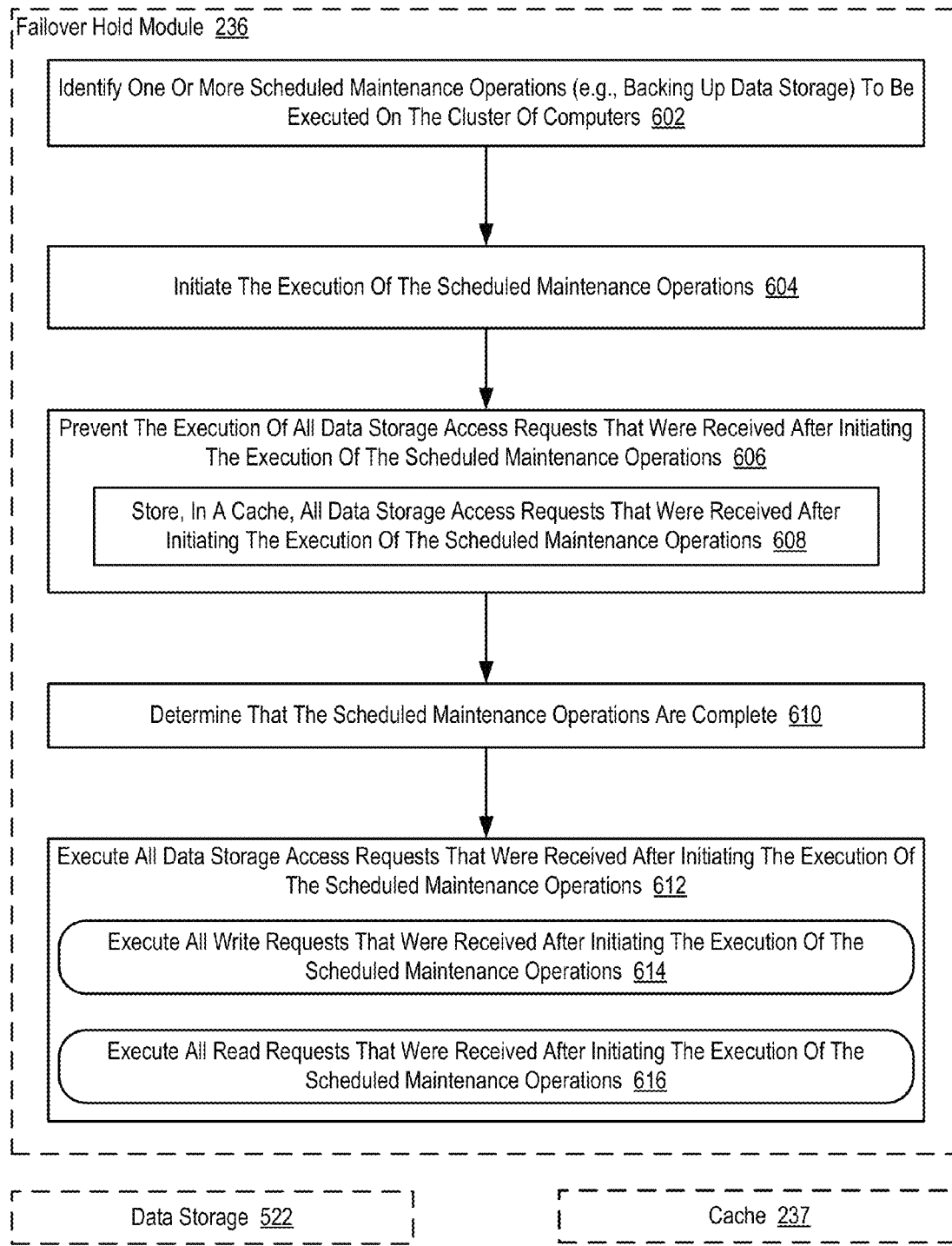
FIG. 6 sets forth a flow chart illustrating an example method of managing maintenance of a cluster of computers according to embodiments of the present invention.

For further explanation, FIG. 6 sets forth a flow chart illustrating an example method of managing maintenance of a cluster of computers according to embodiments of the present invention. The example method of FIG. 6 includes identifying (602), by a failover hold module (236), one or more scheduled maintenance operations to be executed on the cluster of computers. In the example of FIG. 6, the one or more scheduled maintenance operations are operations designed to keep the cluster of computers operating at expected performance levels. Examples of scheduled maintenance operations include, for example, backing up data, performing software updates, executing anti-virus software, and so on. In the example method of FIG. 6, the one or more scheduled maintenance operations to be executed on the cluster of computers can include backing up data storage (522) on the cluster of computers. Backing up data storage (522) on the cluster of computers may be carried out, for example, by copying all data contained in data storage (522) on the cluster of computers to off-site memory.

The example method of FIG. 6 also includes initiating (604) the execution of the scheduled maintenance operations. Initiating (604) the execution of the scheduled maintenance operations may be carried out, for example, by executing a software module that carries out maintenance operations. For example, a software module that performs a data backup may be executed to initiate (604) data backup maintenance operations, a software module that performs an operating system update may be executed to initiate (604) system update maintenance operations, and so on.

The example method of FIG. 6 also includes, without (606) reporting an error, preventing the execution of all data storage (522) access requests that were received after initiating the execution of the scheduled maintenance operations. In the example of FIG. 6, preventing the execution of all data storage (522) access requests that were received after initiating the execution of the scheduled maintenance operations may be carried out by delaying the dispatch of the data storage (522) access requests for execution. For example, if data storage (522) was being backed up to off-site memory, executing a data storage (522) access request may result in data storage (522) being altered such that the backup of the data storage (522) is out-of-date before the backup has even completed. As such, the failover hold module (236) may 'hold' all of the data storage (522) access requests until a point in time at which the backup of data storage (522) has completed.

In the example method of FIG. 6, preventing the execution of all data storage access requests that were received after initiating the execution of the scheduled maintenance operations can include storing (608), in a cache (237), all data storage (522) access requests that were received after initiating the execution of the scheduled maintenance operations. In the example of FIG. 6, the cache (237) represents a component of data storage that is distinct from the data storage (522) that the data storage (522) access request was directed to. In such an example, rather than attempting to execute an access of the data storage (522) of a system that is executing maintenance operations, the failover hold module (236) may instead store (608) all data storage (522) access requests that were received after initiating the execution of the scheduled maintenance operations in the cache (237) so that the data storage (522) access requests may be executed upon the completion of the maintenance operations.

The example method of FIG. 6 also includes determining (610) that the scheduled maintenance operations are complete. In the example of FIG. 6, determining (610) that the scheduled maintenance operations are complete may be carried out, for example, by receiving a notification indicating that the scheduled maintenance operations, by the expiration of a predetermined time period since the scheduled maintenance operations began, by identifying the processes executing on a particular computer in the cluster of computers and determining that the all processes that are part of the scheduled maintenance operations are no longer executing, and in other ways as will occur to those of skill in the art.

The example method of FIG. 6 also includes executing (612) all data storage (522) access requests that were received after initiating the execution of the scheduled maintenance operations. In the example of FIG. 6, executing (612) all data storage (522) access requests that were received after initiating the execution of the scheduled maintenance operations may be carried out, for example, by retrieving the data storage (522) access requests that were received after initiating the execution of the scheduled maintenance operations from the cache (237). In such an example, executing (612) all data storage (522) access requests that were received after initiating the execution of the scheduled maintenance operations may further be carried out by dispatching such data storage (522) access requests for execution after the data storage (522) access requests have been retrieved from the cache (237).

In the example method of FIG. 6, a data storage (522) access request may be embodied as a write operation. In such an example, executing (612) all data storage (522) access requests that were received after initiating the execution of the scheduled maintenance operations can include executing (614) all write requests that were received after initiating the execution of the scheduled maintenance operations. In the example of FIG. 6, a data storage (522) access request may also be embodied as a write operation. In such an example, executing (612) all data storage (522) access requests that were received after initiating the execution of the scheduled maintenance operations can also include executing (616) all read requests that were received after initiating the execution of the scheduled maintenance operations.

As mentioned above, a cloud computing environment useful in embodiments of the present invention is generally considered service oriented with a focus on statelessness, low coupling, modularity, and semantic interoperability. At the heart of cloud computing is an infrastructure comprising a network of interconnected nodes. For further explanation, FIG. 7 sets forth a block diagram of an example of a cloud computing node useful according to embodiments of the present invention. Cloud computing node (10) is only one example of a suitable cloud computing node and is not intended to suggest any limitation as to the scope of use or functionality of embodiments of the invention described herein. Regardless, cloud computing node (10) is capable of being implemented and/or performing any of the functionality set forth hereinabove.

The cloud computing node (10) is operational with numerous other general purpose or special purpose computing system environments or configurations. Examples of well-known computing systems, environments, and/or configurations that may be suitable for use with the cloud computing node (10) include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The cloud computing node (10) may be described in the general context of computer system-executable instructions, such as program modules, being executed by a computer system. Generally, program modules may include routines, programs, objects, components, logic, data structures, and so on that perform particular tasks or implement particular abstract data types. The cloud computing node (10) may be practiced in distributed cloud computing environments where tasks are performed by remote processing devices that are linked through a communications network. In a distributed cloud computing environment, program modules may be located in both local and remote computer system storage media including memory storage devices.

Figure 7:
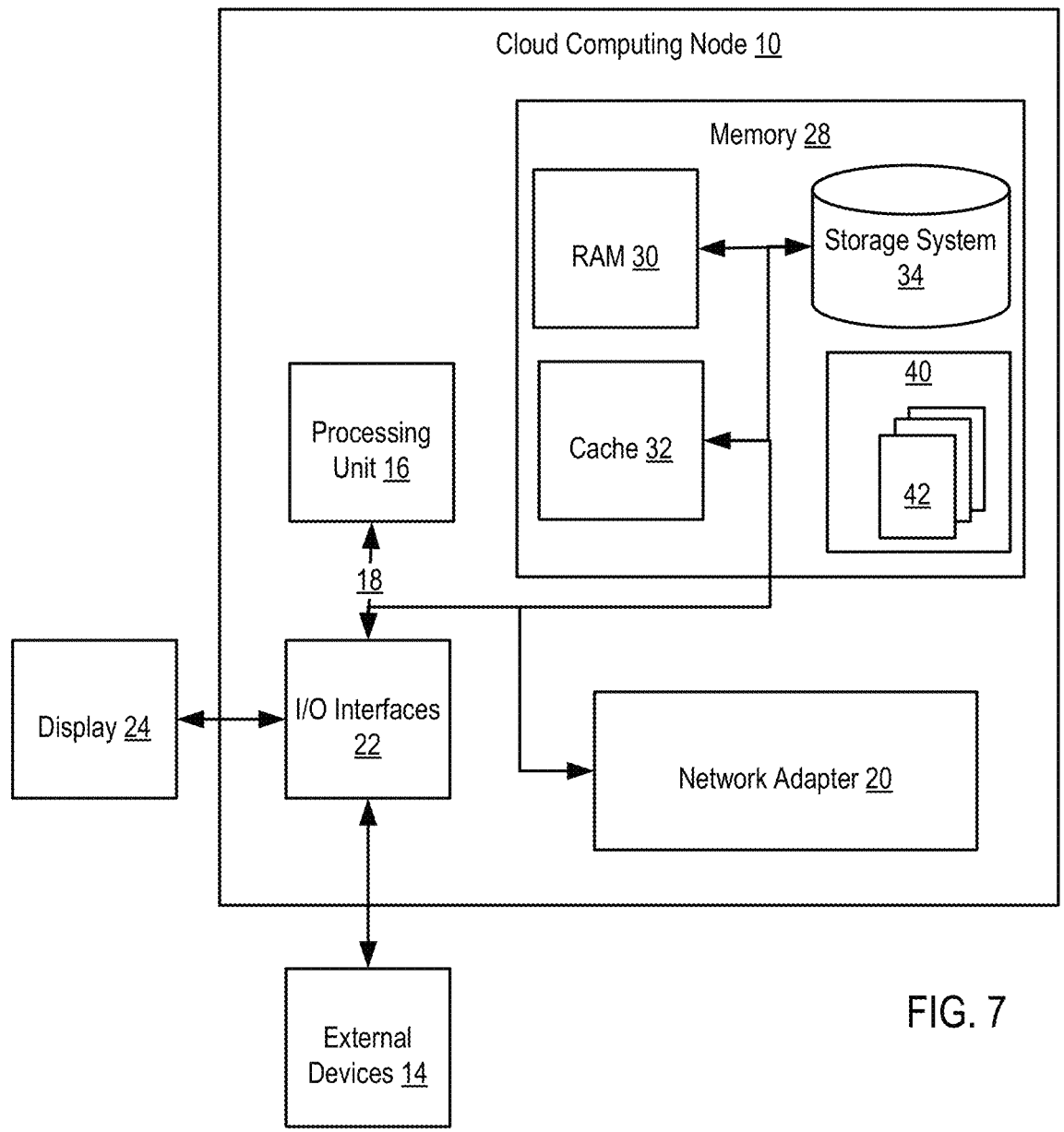
FIG. 7 sets forth a block diagram of an example of a cloud computing node useful according to embodiments of the present invention.

As shown in FIG. 7, the cloud computing node (10) is shown in the form of a general-purpose computing device. The components of the cloud computing node (10) may include, but are not limited to, one or more processors or processing units (16), a system memory (28), and a bus (18) that couples various system components including the system memory (28) to the processor (16).

The bus (18) in the example of FIG. 7 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture ('ISA') bus, Micro Channel Architecture ('MCA') bus, Enhanced ISA ('EISA') bus, Video Electronics Standards Association ('VESA') local bus, and Peripheral Component Interconnects ('PCI') bus.

The cloud computing node (10) of FIG. 7 often includes a variety of computer system readable media. Such media may be any available media that is accessible by the cloud computing node (10), and it includes both volatile and non-volatile media, removable and non-removable media.

The system memory (28) in the example of FIG. 7 can include computer system readable media in the form of volatile memory, such as random access memory ('RAM') (30) and/or cache memory (32). The cloud computing node (10) may further include other removable/non-removable, volatile/non-volatile computer system storage media. By way of example only, a storage system (34) can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, the memory (28) may include at least one program product having a set (e.g., at least one) of program modules that are configured to carry out the functions of embodiments of the invention.

The example of FIG. 7 includes a program/utility (40) having a set (at least one) of program modules (42) that may be stored in the memory (28). The cloud computing node (10) of FIG. 7 may also include an operating system, one or more application programs, other program modules, and program data. Each of the operating system, one or more application programs, other program modules, and program data or some combination thereof, may include an implementation of a networking environment. Program modules (42) generally carry out the functions and/or methodologies of embodiments of the invention as described herein.

The cloud computing node (10) of FIG. 7 may also communicate with one or more external devices (14) such as a keyboard, a pointing device, a display (24), and so on that enable a user to interact with the cloud computing node (10). The cloud computing node (10) may also include any devices (e.g., network card, modem, etc.) that enable the cloud computing node (10) to communicate with one or more other computing devices. Such communication can occur, for example, via I/O interfaces (22). Still yet, the cloud computing node (10) can communicate with one or more networks such as a local area network (IAN), a general wide area network ('WAN'), and/or a public network (e.g., the Internet) via network adapter (20). As depicted, network adapter (20) communicates with the other components of the cloud computing node (10) via the bus (18). It should be understood that although not shown, other hardware and/or software components could be used in conjunction with the cloud computing node (10). Examples include, but are not limited to, microcode, device drivers, redundant processing units, external disk drive arrays, RAID systems, tape drives, and data archival storage systems, and so on.

Figure 8:
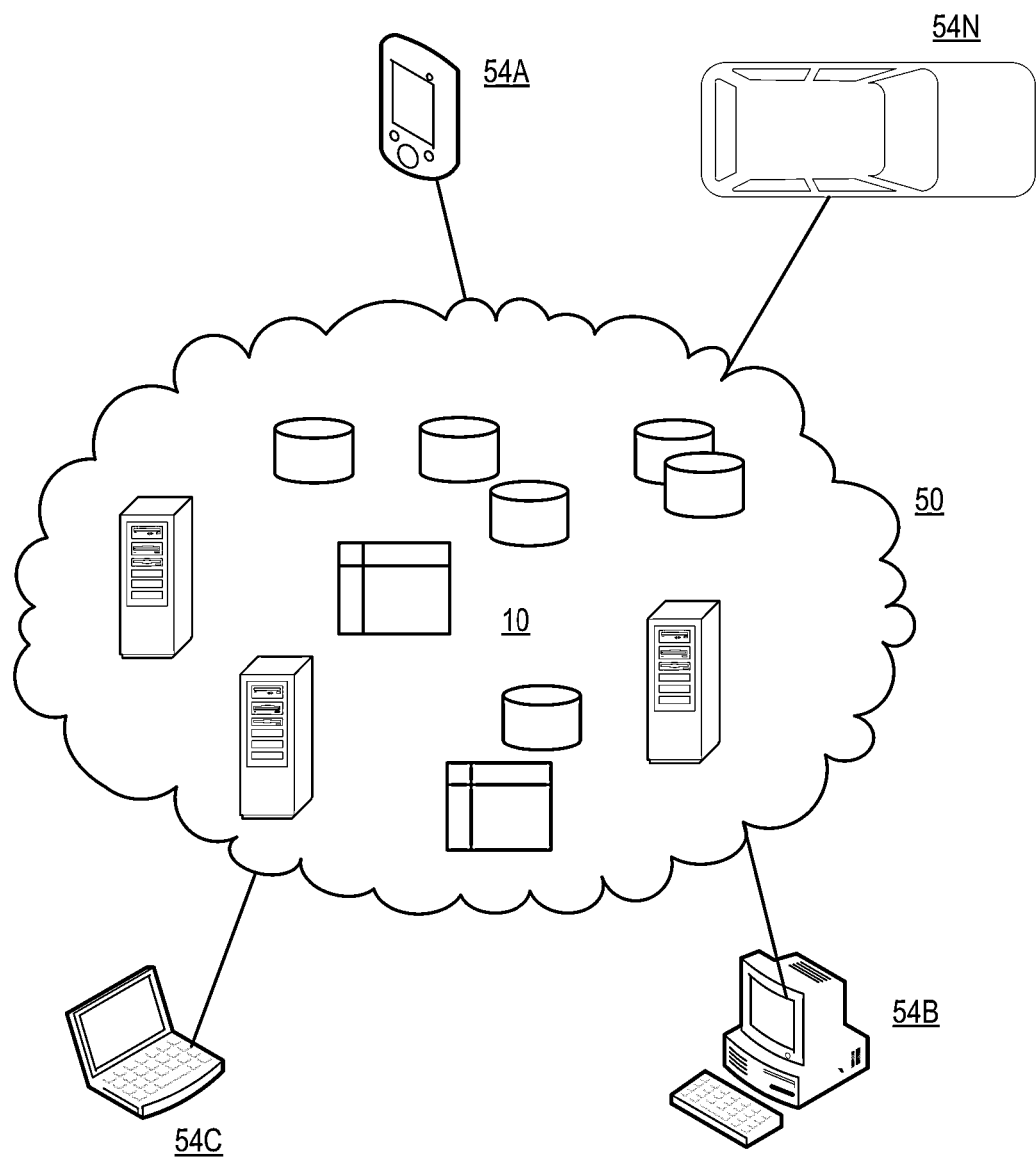
FIG. 8 sets forth a line drawing of an example cloud computing environment.

For further explanation, FIG. 8 sets forth a line drawing of an example cloud computing environment (50). The cloud computing environment (50) of FIG. 8 comprises one or more cloud computing nodes (10) with which local computing devices used by cloud consumers, such as, for example, personal digital assistant (PDA) or cellular telephone (54A), desktop computer (54B), laptop computer (54C), and/or automobile computer system (54N) may communicate. The cloud computing nodes (10) may communicate with one another. They may be grouped (not shown) physically or virtually, in one or more networks, such as private, community, public, or hybrid clouds as described hereinabove, or a combination thereof. This allows cloud computing environment (50) to offer infrastructure, platforms and/or software as services for which a cloud consumer does not need to maintain resources on a local computing device. It is understood that the types of computing devices (54A-N) shown in FIG. 8 are intended to be illustrative only and that computing nodes (10) and cloud computing environment (50) can communicate with any type of computerized device over any type of network and/or network addressable connection (e.g., using a web browser).

Figure 9:
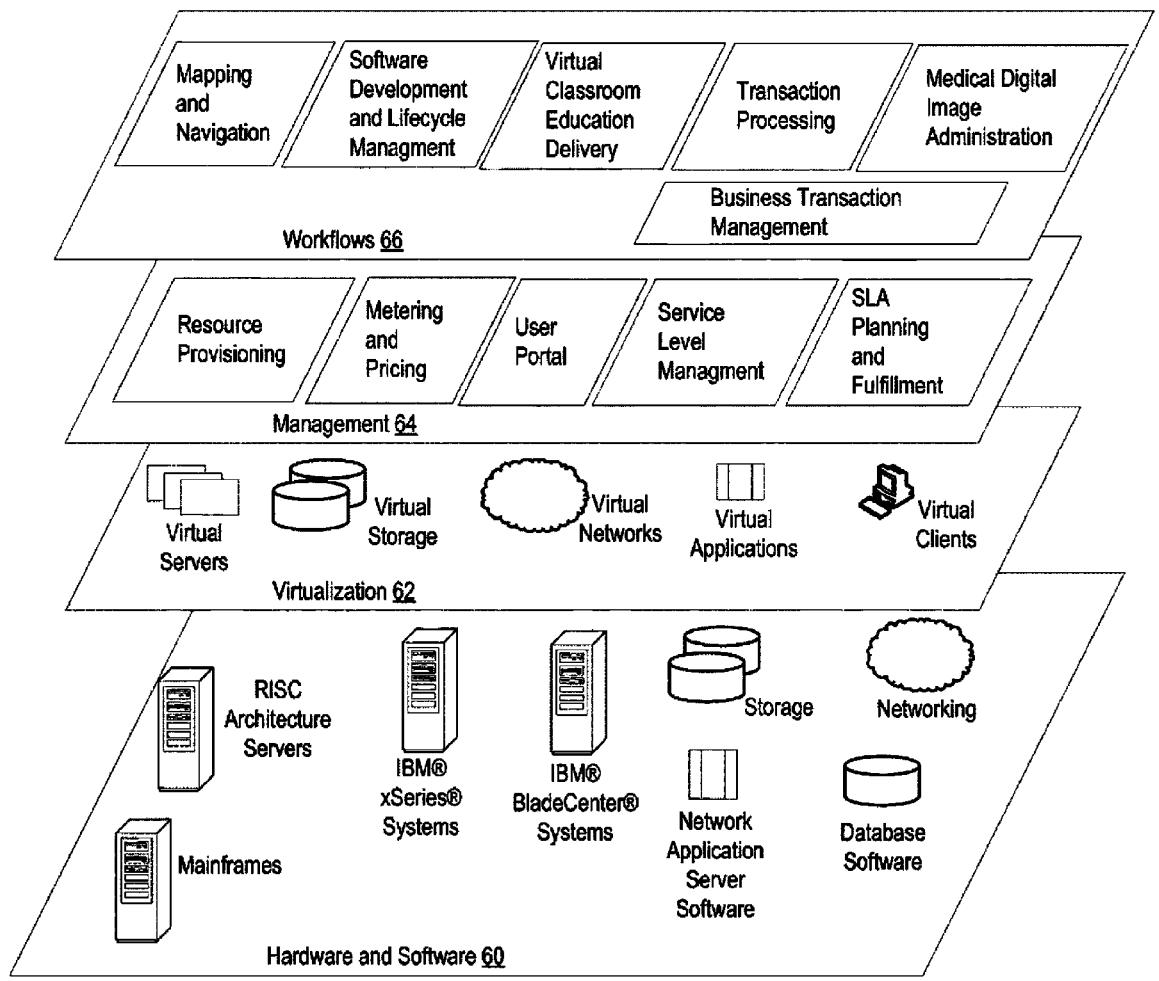
FIG. 9 sets forth a line drawing showing an example set of functional abstraction layers provided by cloud computing environment.

For further explanation, FIG. 9 sets forth a line drawing showing an example set of functional abstraction layers provided by cloud computing environment (50 in FIG. 8). It should be understood in advance that the components, layers, and functions shown in FIG. 9 are intended to be illustrative only and embodiments of the invention are not limited thereto. As depicted, the following layers and corresponding functions are provided:

The example of FIG. 9 includes a hardware and software layer (60). Hardware and software layer (60) in the example of FIG. 9 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide)

The example of FIG. 9 includes a virtualization layer (62). The virtualization layer (62) of FIG. 9 provides an abstraction layer from which the following examples of virtual entities may be provided: virtual servers; virtual storage; virtual networks, including virtual private networks; virtual applications and operating systems; and virtual clients.

The example of FIG. 9 also includes a management layer (64). The management layer (64) may provide the functions described below. Resource provisioning provides dynamic procurement of computing resources and other resources that are utilized to perform tasks within the cloud computing environment. Metering and pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

The example of FIG. 9 also includes a workflows layer (66). The workflows layer (66) of FIG. 9 provides examples of functionality for which the cloud computing environment may be utilized. Examples of workflows and functions which may be provided from this layer include: mapping and navigation; software development and lifecycle management; virtual classroom education delivery; data analytics processing; and transaction processing.

The workflows layer (66) can manage failover operations on a cluster of computers, including: identifying, by a failover hold module, a failure to access data storage in the cluster of computers; preventing the execution of all read operations directed to the data storage that were received after the failure to access data storage was identified; executing all write operations directed to the data storage that were received after the failure to access data storage was identified, including writing data to a cache; identifying that a failover to alternative data storage is complete; executing the held read operations, including reading data from the alternative data storage; and copying, from cache to the alternative data storage, the data written to the cache as part of the write operations.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A method of managing failover operations on a cluster of computers, the method comprising:
   identifying, by a failover hold module, a failure to access data storage in the cluster of computers;
   in response to identifying the failure to access data storage:
      holding all read operations directed to the data storage; and
      executing all write operations directed to the data storage by redirecting the write operations to a cache;
   identifying that a failover to an alternative data storage is complete;
   in response to identifying that the failover to the alternative data storage is complete:
      copying, from cache to the alternative data storage, the data written to the cache as part of execution of the write operations; and
      executing held read operations by reading data from the alternative data storage instead of the data storage to which the read operation is directed.

2. The method of claim 1 wherein identifying a failure to access data storage includes identifying that a read operation failed.

3. The method of claim 1 wherein identifying a failure to access data storage includes identifying that a write operation failed.

4. The method of claim 1 wherein identifying a failure to access data storage includes identifying a failure to access a file system.

5. The method of claim 1 wherein identifying a failure to access data storage includes identifying a failure to access a database.

6. A method of managing maintenance of a cluster of computers, the method comprising:
- identifying, by a failover module, one or more scheduled maintenance operations to be executed on the cluster of computers;
- initiating the execution of the scheduled maintenance operations;
- in response to initiating the execution of the scheduled maintenance operations, holding all received data storage access requests;
- determining that the scheduled maintenance operations are complete; and
- in response to determining that the scheduled maintenance operations are complete, executing all held data storage access requests including executing all write requests that were received after initiating the execution of the scheduled maintenance operations.

7. The method of claim 6 wherein holding all received data storage access requests further comprises storing, in a cache, all data storage access requests that were received after initiating the execution of the scheduled maintenance operations.

8. The method of claim 6 wherein executing all held data storage access requests includes executing all read requests that were received after initiating the execution of the scheduled maintenance operations.

9. The method of claim 6 wherein the one or more scheduled maintenance operations to be executed on the cluster of computers includes backing up data storage on the cluster of computers.

\* \* \* \* \*